United States Patent
Longhini et al.

(10) Patent No.: US 7,828,740 B2
(45) Date of Patent: Nov. 9, 2010

(54) NONINVASIVE APPARATUS AND METHOD FOR ESTIMATING BLOOD PRESSURE

(75) Inventors: Luca Longhini, Ferrara (IT); Lorenzo Peretto, Fratta Polesine (IT)

(73) Assignee: Luca Longhini, Ferrara (IT)

( * ) Notice: Subject to any disclaimer, the term of this patent is extended or adjusted under 35 U.S.C. 154(b) by 1135 days.

(21) Appl. No.: 11/496,754

(22) Filed: Aug. 1, 2006

(65) Prior Publication Data

US 2007/0032728 A1 Feb. 8, 2007

Related U.S. Application Data

(60) Provisional application No. 60/704,921, filed on Aug. 3, 2005.

(51) Int. Cl.
*A61B 5/02* (2006.01)

(52) U.S. Cl. .................................................. 600/528

(58) Field of Classification Search ................ 600/485, 600/493–496, 508, 513, 514, 528, 586
See application file for complete search history.

(56) References Cited

U.S. PATENT DOCUMENTS

| 6,050,950 | A * | 4/2000 | Mohler ....................... 600/485 |
| 6,368,283 | B1 * | 4/2002 | Xu et al. ..................... 600/485 |
| 2004/0167417 | A1 | 8/2004 | Schulhauser et al. | |

OTHER PUBLICATIONS

A New Noninvasive Method for Estimation of Pulmonary Arterial Pressure in Mitral Stenosis; by: Carlo Longhini, et al.; The American Journal of Cardiology vol. 68, (Aug. 1, 1991) pp. 398-401.
A new, simple, and accurate method for non-invasive estimation of pulmonary arterial pressure; J. Xu et al.; www.hearjnl.com, (Heart 2002) vol. 88; pp. 76-80.
Noninvasive Estimation of the Pulmonary Systolic Pressure From the Spectral Analysis of the Second Heart Sound; S. Aggio et al.; Acta Cardiologica, vol. XLV, 1990, 3 pp. 199-202.
Estimation of Pulmonary Artery Pressure by Spectral Analysis of the Second Heart Sound; Danmin Chen, et al.; The American Journal of Cardiology, vol. 78, (Oct. 1, 1996) pp. 785-789.
International Search Report Corresponding to PCT/IB2007/004048 dated Jul. 10, 2008.
B. Popov et al., "Automated Extraction of Aortic and Pulmonary Components of the Second Heart Sound for the Estimation of Pulmonary Artery Pressure," Conference Proceedings. 26th Annual International Conference of the IEEE Engineering in Medicine and Biology Society (IEEE Cat. No. 04CH37558) IEEE Piscataway, NJ, USA. vol. 2, 2004, pp. 921-924. ISBN: 0-7803-8439-3.
International Search Report for PCT International Application No. PCT/IB2006/002111 mailed Jan. 24, 2007.

* cited by examiner

*Primary Examiner*—Mark W Bockelman
*Assistant Examiner*—Roland Dinga
(74) *Attorney, Agent, or Firm*—RatnerPrestia

(57) ABSTRACT

Methods and apparatus for noninvasively estimating a blood pressure are provided. A pulmonic (P) component extracted from a second heart sound (S2) signal is analyzed to obtain a number of oscillations in the P component. A predetermined relationship between the number of oscillations and PAP is used to generate a blood pressure estimate. A PCG sensor including a mechanical filter for receiving heart sounds from a chest wall is also provided. The pressure of the PCG sensor on the chest wall is adjustable.

23 Claims, 13 Drawing Sheets

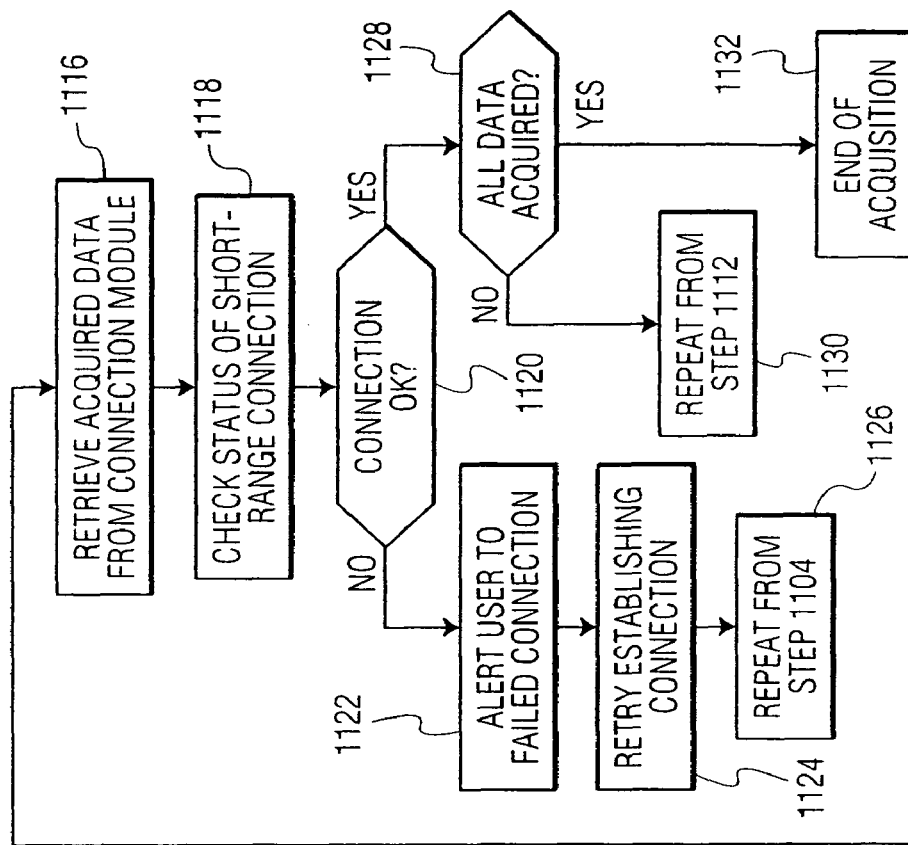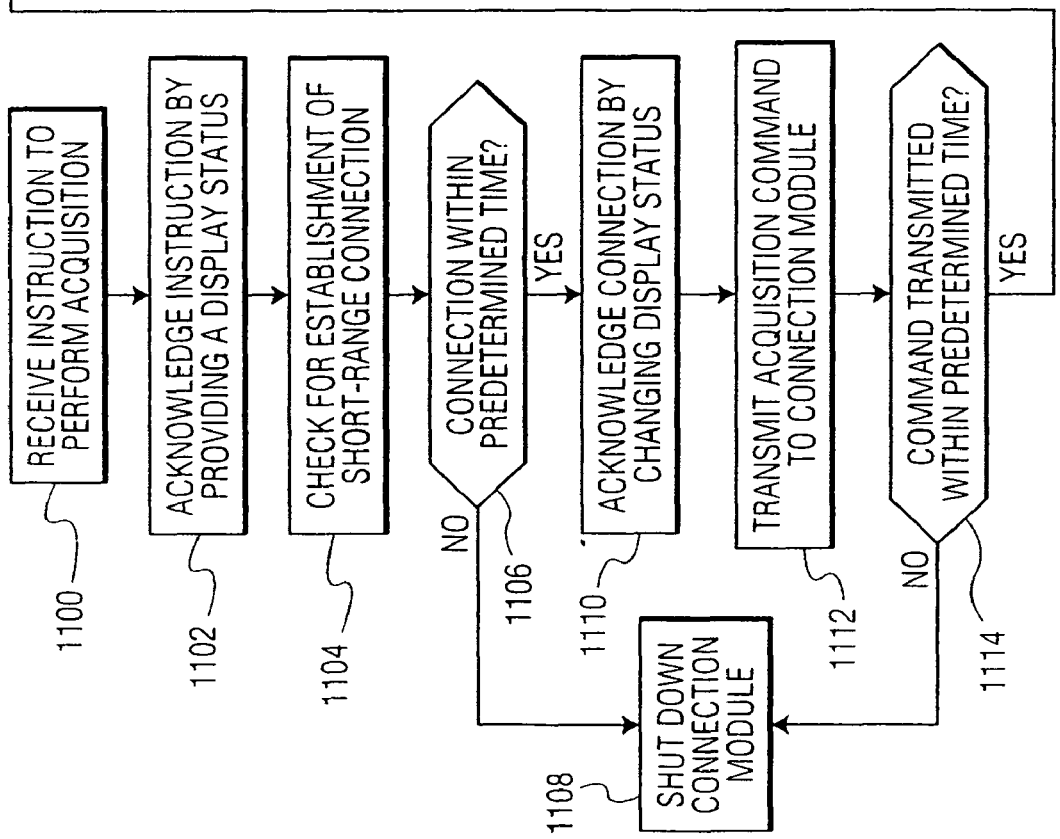
FIG. 11

NONINVASIVE APPARATUS AND METHOD FOR ESTIMATING BLOOD PRESSURE

CROSS REFERENCE TO RELATED APPLICATIONS

This application is related to and claims the benefit of U.S. Provisional Application No. 60/704,921 entitled NONINVASIVE APPARATUS FOR THE PULMONARY ARTERY PRESSURE MEASUREMENT filed on Aug. 3, 2005, the contents of which are incorporated herein by reference.

FIELD OF THE INVENTION

The present invention relates to the field of clinical evaluation of cardiac diseases and, more particularly, to methods and apparatus for noninvasively estimating the pulmonary artery pressure.

BACKGROUND OF THE INVENTION

Pulmonary artery pressure (PAP) measurements are known in the art and have been used for a number of years to aid in the diagnosis of cardiac and pulmonary diseases. A PAP measurement may be obtained through an invasive procedure, such as using a pulmonary arterial catheter (e.g. Swan-Ganz catheter). A PAP estimation may also be obtained through a noninvasive procedure, for example, using Doppler Echocardiography, in order to estimate the PAP via known-in-the-art ultrasound techniques. In addition, methods using heart sounds analysis have also been proposed. For example, see U.S. Pat. No. 6,368,283 to Xu et al., entitled "Method and apparatus for estimating systolic and mean pulmonary artery pressures of a patient."

Invasive procedures, however, are typically uncomfortable for the patient. Pulmonary artery catheterization, for example, even in skilled hands, may carry various risks and complications.

Doppler Echocardiography, may not be efficacious in the absence of a Doppler-detectable tricuspid valve regurgitation. Furthermore, the values of systolic PAP are only approximate because a clinical estimation of the right atrial (RA) pressure is typically necessary. This may be a potential source of error in the estimation of the real PAP in a patient. Furthermore, a good acoustic window and satisfactory flow tracing are typical factors used to adequately locate the tricuspid regurgitant jet. These factors, however, may be suboptimal in persons with pulmonary hyperinflation, or in those persons who are obese, because of poor transmission of sound waves.

Both conventional invasive and noninvasive procedures typically require highly skilled personnel (i.e. physicians or technicians) as well as the utilization of expensive equipment. Cardiac catheterization may also require use of a suitably equipped operating room, with attending operating room personnel.

SUMMARY OF THE INVENTION

The present invention is embodied in a method and apparatus for noninvasively estimating a blood pressure. The method includes the steps of a) extracting a pulmonic (P) component from a second heart sound (S2) signal and b) analyzing the extracted P component to obtain a number of oscillations in the P component. The method further includes the step of c) applying a predetermined relationship between the obtained number of oscillations and blood pressure to generate a blood pressure estimate.

The present invention is further embodied in an apparatus for receiving heart sounds from a chest wall. The apparatus includes a sensor coupled to the chest wall and configured to receive heart sounds from the chest wall and a cover disposed over the sensor and coupled to the chest wall. The apparatus further includes adjusting means for adjusting the pressure of the sensor on the chest wall within the cover and holding means for coupling the cover to the chest wall. The holding means and the cover tend to increase a transmission of the heart sounds from the chest wall to the sensor relative to the sensor without the holding means or the cover.

BRIEF DESCRIPTION OF THE DRAWINGS

The invention is best understood from the following detailed description when read in connection with the accompanying drawings. It is emphasized that, according to common practice, various features/elements of the drawings may not be drawn to scale. On the contrary, the dimensions of the various features/elements may be arbitrarily expanded or reduced for clarity. Moreover in the drawings, common numerical references are used to represent like features/elements. Included in the drawing are the following figures:

FIG. 11 is a flow chart illustrating an exemplary method for performing data acquisition using an exemplary connection module shown in FIG. 10, according to an embodiment of the present invention.

DETAILED DESCRIPTION OF THE INVENTION

The present invention describes methods and apparatus for noninvasively estimating blood pressure and, desirably, PAP. First, an exemplary system for estimating PAP is described. Second, an exemplary PCG sensor is described. Third, exemplary ECG and PCG signal conditioners are described. Fourth, methods for noninvasively estimating PAP are described. Fifth, an exemplary connection module of a data acquisition system is described. Sixth, a method for performing data acquisition using a short-range connection is described.

According to the present invention, PAP may be estimated by simultaneously measuring electrocardiogram (ECG) and phonocardiogram (PCG) signals from respective ECG and PCG sensors. A second heart sound (S2) signal may be extracted from the PCG signal using the QRS complex of the ECG signal. A number of oscillations of the pulmonary (P) component, extracted from the S2 signal, is desirably determined using the time-domain S2 signal. A PAP estimate may be generated using a predetermined relationship between the number of oscillations and the PAP. In an exemplary embodiment, the PCG sensor desirably includes a mechanical filter, adjusting means and holding means to reduce background noise and increase the transmission of heart sounds to the PCG sensor. In a further exemplary embodiment, a number of PCG and corresponding ECG signals are acquired and analyzed in order to generate the PAP estimate. Although the present invention describes methods and apparatus for PAP estimation, it is contemplated that the present invention may be used for any blood pressure measurement, PAP being only one example of such a blood pressure measurement. It is contemplated that a predetermined relationship may be determined between the number of oscillations and blood pressure to determine a blood pressure estimate.

Figure 1A:
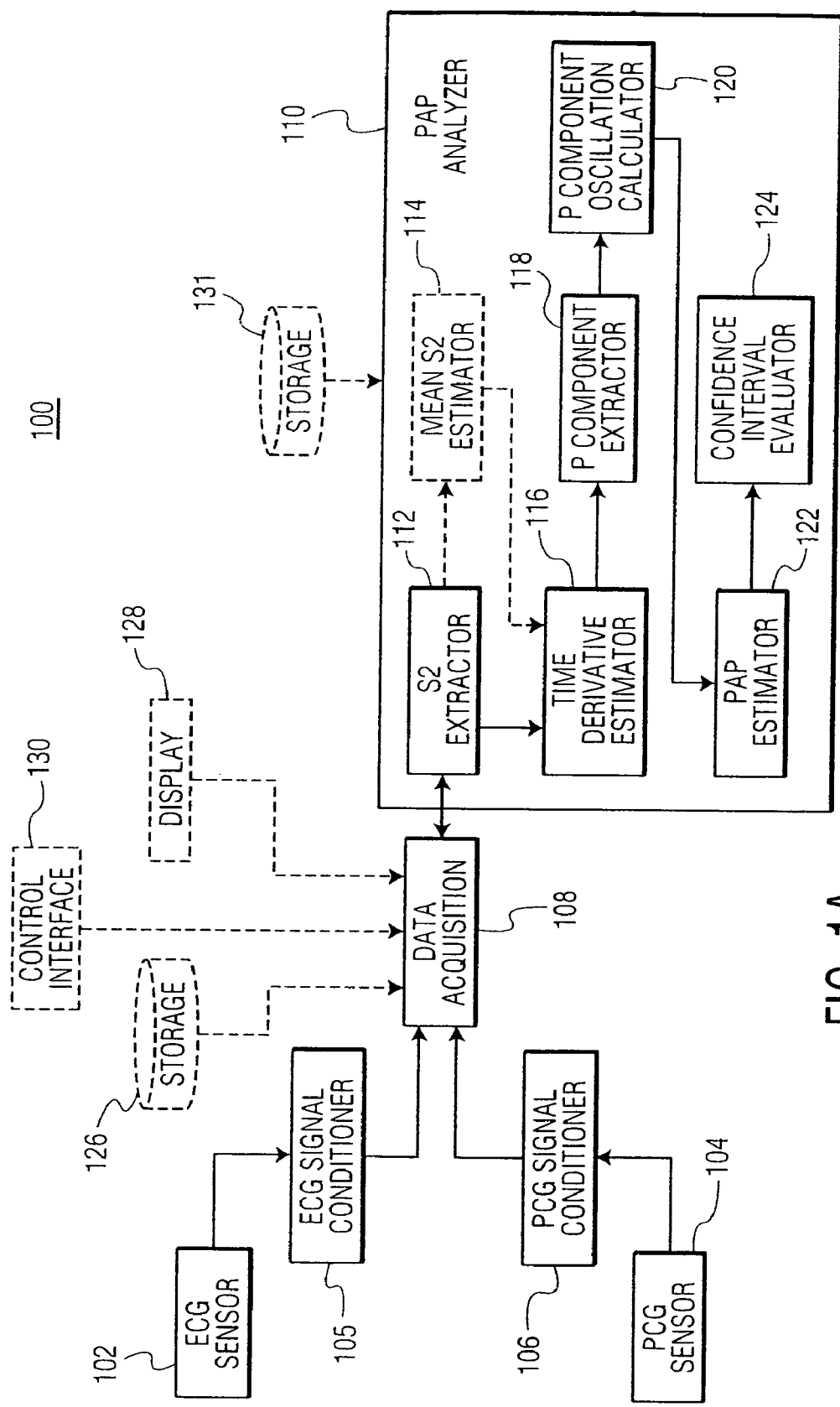
FIGS. 1A, 1B and 1C are functional block diagrams illustrating an exemplary apparatus for noninvasively estimating a pulmonary artery pressure (PAP) according to an embodiment of the present invention.
Figure 1B:
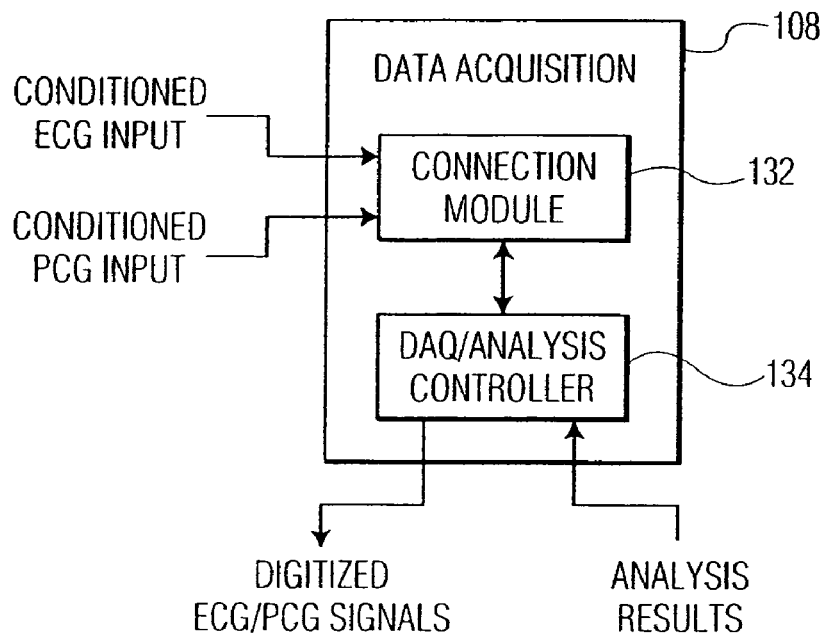
Figure 1C:
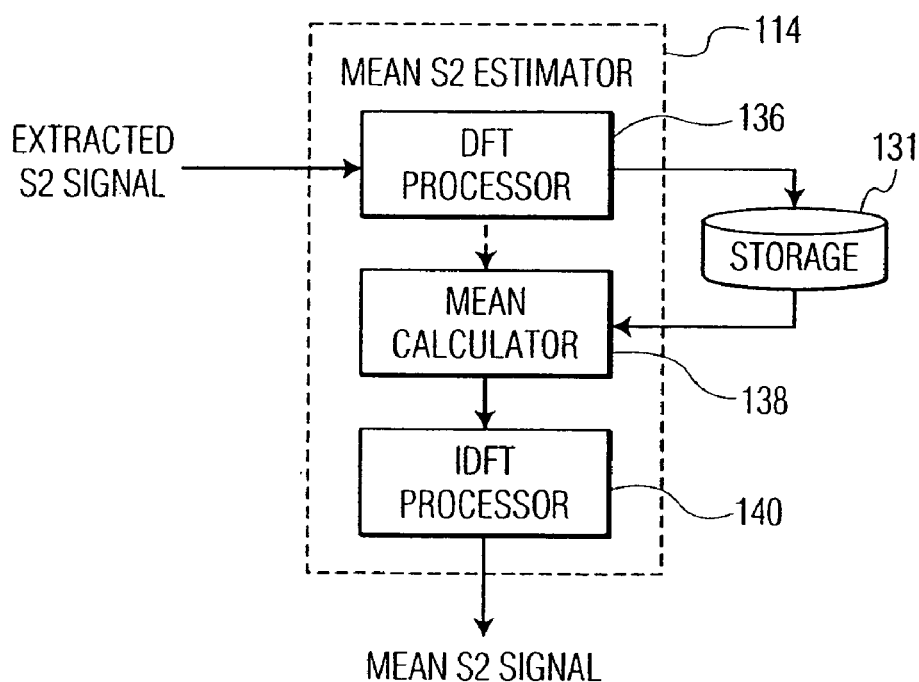

FIGS. 1A, 1B and 1C are functional block diagrams illustrating an exemplary apparatus 100 for noninvasively estimating a PAP according to an embodiment of the present invention. More particularly, FIG. 1A is a functional block diagram of exemplary apparatus 100; FIG. 1B is a functional block diagram of data acquisition system 108; and FIG. 1C is a functional block diagram of mean S2 estimator 114.

Referring to FIG. 1A, an ECG signal from ECG sensor 102 is provided to ECG signal conditioner 105 (described further below) and subsequently the conditioned ECG signal is provided to a data acquisition system 108. A PCG signal from PCG sensor 104 is provided to PCG signal conditioner 106 (described further below) and subsequently the conditioned PCG signal is provided to data acquisition system 108. The PCG signal is desirably synchronously acquired with the ECG signal by data acquisition system 108.

The ECG signal is typically a multilead ECG signal. In an exemplary embodiment ECG sensor 102 consists of three electrodes having three-leads transmitted to the ECG signal conditioner 105. It is understood that the ECG sensor 102 may include any desired number of electrodes for obtaining appropriate ECG signals for determining a QRS complex. It is understood that the ECG electrodes are provided at suitable locations on the chest wall for obtaining the multilead ECG signal. The PCG sensor 104 is described further below with respect to FIG. 2A.

Data acquisition system 108 acquires and digitizes the conditioned ECG and PCG signals and provides the signals to PAP analyzer 110. The PAP analyzer 110 desirably generates a PAP estimate using the digitized PCG and corresponding digitized ECG signals received from the data acquisition system 108.

In an exemplary embodiment, the data acquisition system 108 and PAP analyzer 110 are configured to connect to a network, including a global information network, e.g. the Internet (not shown) for respectively transmitting and receiving the digitized ECG and PCG signals, as well as transmitting a PAP estimate, an extracted S2 signal, a P component and a confidence interval (described further below) to the data acquisition system 108 by the PAP analyzer 110. It is contemplated, however, that the data acquisition system 108 may be connected to the PAP analyzer 110 via any wired or wireless connection.

Although FIG. 1A illustrates a single input port to PAP analyzer 110 for receiving the digitized ECG and digitized PCG signals, it is contemplated that PAP analyzer 110 may include multiple input ports each capable of receiving one or more of the digitized ECG and digitized PCG signals. It is further contemplated that PAP analyzer 110 may further perform some or all of the acquisition and digitization functions of the data acquisition system 108.

The data acquisition system 108 may optionally include storage means 126 for storing, for example, the PAP estimate, an extracted S2 signal (described further below), a P component, the digitized PCG signal and/or the digitized ECG signal. It is contemplated that storage means 126 may be a memory, a magnetic disk, a database or a further storage means on a remote device, such as a device corresponding to the display 128.

The data acquisition system 108 may optionally include a display 128 for presenting, for example, the PAP estimate, an extracted S2 signal (described further below), a P component, the digitized PCG signal and/or the digitized ECG signal. The display 128 may further present control parameters for controlling the data acquisition. Control parameters may include, for example, an acquisition period duration, a number of PCG and ECG signals to be acquired and an exemplary method (described further below) for obtaining a PAP estimate from a plurality of acquired PCG and ECG signals. The display 128 may include one or more light emitting diodes (LEDs) for providing visual confirmation or error notification during the data acquisition process. It is contemplated that display 128 may include any display capable of presenting information including textual and/or graphical information. Although not shown, the data acquisition system 108 may also include and audio output for providing audible confirmation or error notification during the data acquisition process.

The data acquisition system 108 may optionally include a control interface 130 for providing control parameters to the data acquisition system 108 and/or for providing further control parameters to the PAP analyzer 110 (not shown), for example, selecting a method for obtaining a PAP estimate. Control interface 130 may further select signals to displayed and/or stored. The control interface may include a pointing device type interface for selecting control parameters, display parameters and/or storage parameters using display 128. Control interface 130 may further include a text interface for entering information regarding the acquired signals as well as patient information and a filename for storing acquired and/or analyzed data in storage means 126.

It is contemplated that the data acquisition system 108 and/or PAP analyzer 110 may be configured to connect to the Internet (not shown) such that the generated PAP estimate, an extracted S2 signal (described further below), a P component, the digitized PCG signal and/or the digitized ECG signal may also be transmitted to a remote location for further processing and/or storage.

In an exemplary embodiment, the PAP analyzer 110 is connected to a global information network (e.g. the Internet) such that the acquired and/or analyzed data may be transmitted to data acquisition system 108. Although in an exemplary embodiment the PAP analyzer 110 includes an Internet connection, it is contemplated that transmission of acquired and analyzed data via an output port of PAP analyzer 110 may be provided by any wireless or wired connection.

In an exemplary embodiment, the PAP analyzer 110 includes a computer that executes Java™ software for generating the PAP estimate and the data acquisition system 108 includes a personal digital assistant (PDA) type computer where the storage means 126, display 128 and control interface 130 may be part of the PDA type computer. It is contemplated that PAP analyzer 110 may include any computer including a processor for generating a PAP estimate from the digitized ECG and digitized PCG signals using an algorithm in accordance with the subject invention. The PAP analyzer 110 may include electronic components and any software suitable for performing at least part of the functions of generating a PAP estimate.

Referring now to FIG. 1B, the data acquisition system 108 includes a connection module 132 for receiving analog conditioned PCG and ECG signals and digitizing the signals, for example with an analog to digital converter (ADC) (not shown). The connection module 132 of the exemplary embodiment configures the data acquisition system 108 to receive a differential ECG signal (described further below) and a PCG signal. It is contemplated that any suitable connection module 132 capable of acquiring and digitizing a differential ECG signal and a PCG signal may be used.

Data acquisition system 108 further includes a data acquisition (DAQ)/analysis controller 134 for controlling data acquisition of the ECG and PCG signals and analysis control for transmitting the digitized PCG and ECG signals to the PAP analyzer 110 and receiving the PAP results from the PAP analyzer 110. The DAQ/analysis controller 134 may also control storage of the results in storage means 126 and presentation of results on display 128. The DAQ/analysis controller 134 may also be coupled to control interface 130 for receiving data acquisition and/or analysis parameters. In an exemplary embodiment, DAQ/analysis controller 134 includes a personal digital assistant (PDA) type computer where the storage means 126, display 128 and control interface 130 may be part of the PDA type computer. In an exemplary embodiment, the received ECG signal is also normalized in the DAQ/analysis controller 134. In an exemplary the DAQ/analysis controller 134 includes software, provided in a LabVIEW™ environment, for performing one or more of the functions of the DAQ/analysis controller. It is contemplated that any suitable controller, such as a personal computer, may be used that is capable of controlling data acquisition, transmitting the acquired data, controlling analysis parameters for PAP analyzer 110 and receiving the analysis results.

In an exemplary embodiment, the data acquisition system 108 acquires the PCG and ECG signals at an 8 kHz sampling rate and for an acquisition period of 2 s. It is contemplated that the sampling rate may be any suitable sampling rate to capture the frequencies of the S2 signal and that the acquisition period may include any acquisition period suitable to acquire at least one S2 signal.

Referring back to FIG. 1A, the PAP analyzer 110 receives digitized PCG and digitized ECG signals from data acquisition system 108. The PAP analyzer includes an S2 extractor that is configured to extract an S2 signal from the received digitized PCG signal using the received digitized ECG signal. In one exemplary embodiment, two consecutive QRS complexes are identified in the digitized ECG signal and used to provide a timing window for extracting the S2 signal from the digitized PCG signal (described further below). The extracted S2 signal is provided to time derivative estimator 116.

Time derivative estimator 116 receives the extracted S2 signal from S2 extractor 112 and estimates a time derivative of the extracted S2 signal (described further below). The time derivative of the S2 signal is provided to P component extractor 118. P component extractor 118 receives the time derivative of the 52 signal and extracts the P component. As described below, the P component extractor 118 may use the time derivative to determine the onset time of the P component within the S2 signal and to select a predetermined portion of the S2 signal as the P component. The extracted P component is provided to P component oscillation calculator 120.

The P component oscillation calculator 120 desirably determines a number of oscillations in the extracted P component received from P component extractor 118 according to a time domain analysis of the P component within the 52 signal. In an exemplary embodiment, the P component extractor provides a time derivative of the P component of the S2 signal (the time domain derivative determined by time derivative estimator 116) to P component oscillation calculator 120. In the exemplary embodiment, the P component oscillation calculator 120 determines the number of oscillations using the time derivative of the P component. The number of oscillations determined by the P component oscillation calculator 120 is provided to PAP estimator 122.

The PAP estimator 122 desirably generates a PAP estimate by applying a predetermined relationship between PAP and the number of oscillations received from P component oscillation calculator 120. The predetermined relationship is described further below. It is contemplated that the predetermined relationship may be stored in storage means 131 and retrieved by PAP estimator 122 during generation of the PAP estimate. The PAP estimate may be provided to storage means 126 and/or display 128.

In an exemplary embodiment, a predetermined number of PCG signals and corresponding ECG signals are acquired from ECG sensor 102 and PCG sensor 104 using data acquisition system 108 and processed by PAP analyzer 110 in order to reduce noise artifacts that may be encountered during a single PCG signal and corresponding ECG signal acquisition. For example, noise artifacts may include respiration, patient movement, sensor movement as well as other physiological sounds and background noise that may be added to the PCG and/or ECG signals during one acquisition period. Accordingly, a predetermined number of PCG and ECG signals may be acquired. In an exemplary embodiment, the predetermined number of PCG and ECG signals includes a range of about 50-70. It is contemplated that fewer or more signals may be acquired and processed depending upon the recording conditions as well as background noise.

In an exemplary embodiment, the PAP analyzer 110 may process the predetermined number of PCG signals and corresponding ECG signals to generate a plurality of PAP estimates. The plurality of PAP estimates may be stored in storage means 131. PAP analyzer 110 may include a confidence interval evaluator 124 to evaluate a confidence interval measure from the plurality of PAP estimates generated using the predetermined number of acquired signals. For example, the confidence interval measure may provide high and low PAP estimates within a confidence interval from the PAP estimates. The confidence interval measure may be provided by interval evaluator 124 to storage means 126 and/or display 128. Although illustrated with respected to a plurality of PAP estimates, it is contemplated that a confidence measure may be provided for a single PAP estimate.

In an alternative embodiment, PAP analyzer 110 may include a mean S2 estimator 114 that may be configured to determine a mean S2 signal by calculating the arithmetic mean of a plurality of extracted S2 signals received from S2 extractor 112, where the plurality of extracted S2 signals corresponds to the predetermined number of acquired signals. Referring to FIG. 1C, each of the extracted S2 signals may be provided to a discrete Fourier transform (DFT) processor 136 to generate a DFT signal of the extracted S2 signal. The DFT signals may be stored in storage means 131. When a predetermined number of S2 signals are extracted, the plurality of DFT signals may be provided to mean S2 calculator 138 in order to calculate a mean DFT signal from the stored plurality of DFT signals. The mean DFT signal is provided to inverse DFT (IDFT) processor 140. IDFT processor 140 desirably generates an IDFT from the mean DFT signal in order to form a time-domain mean S2 signal.

It is contemplated that mean S2 calculator 138 may include an accumulator (not shown) and that each DFT signal may be directly provided to the accumulator rather than to storage means 131 in order to generate a summation of the DFT signals as they are generated. The mean S2 calculator 138 may further include a multiplier for generating a mean DFT signal from the summed DFT signals provided by the accumulator.

Referring back to FIG. 1A, the mean S2 signal may be provided to time derivative estimator 116 and processing through PAP analyzer 110 blocks 116-122 may continue as described above using the mean S2 signal determined by mean S2 estimator 114.

Figure 2A:
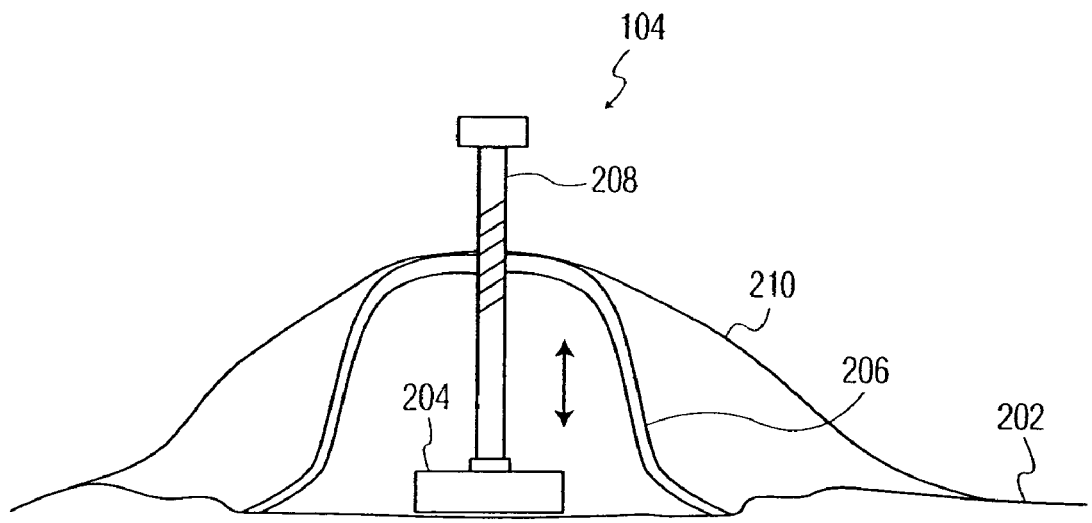
FIG. 2A is a cut-away side plan drawing illustrating an exemplary phonocardiogram (PCG) sensor shown in FIG. 1A, according to an embodiment of the present invention.

FIG. 2A is a cut-away side plan drawing illustrating an exemplary PCG sensor 104 (FIG. 1A) for receiving heart sounds, according to an embodiment of the present invention. A sensor 204 is desirably coupled to receive heart sounds through chest wall 202. The sensor 204 is desirably provided within a cover 206 that may act as a mechanical filter. In an exemplary embodiment, sensor 204 is a piezoelectric transducer available from BIOPAC Systems, Inc., model number SS17L. It is contemplated that sensor 204 may be any sensor capable of receiving heart sounds and transducing the heart sounds into an electrical signal where the sensor has a sensitivity and frequency range suitable for transducing heart sounds.

In an exemplary embodiment, the cover 206 is a bell-shaped cover 206 disposed over the sensor. A lip of the cover 206 is desirable coupled to the chest wall in order to increase a transmission of heart sounds from the chest wall 202 to the sensor 204. The cover 206 also desirably attenuates background noise transmitted to the sensor 204. By coupling cover 206 to the chest wall 202, the cover 206 may mitigate a low-pass filter effect on the transmitted heart sounds by the underlying tissue (i.e. below chest wall 202). Although cover 206 is illustrated as being bell-shaped, it is contemplated that the cover 206 may be any suitably shaped cover capable of reducing background noise and increasing a transmission of the heart sounds to the sensor 204.

The pressure of the sensor 204 on the chest wall 202 is desirably adjusted using adjusting means 208. By adjusting the pressure, a coupling, and thus the fidelity of heart sound transmission to the sensor 204 may be increased. In an exemplary embodiment, adjusting means 208 includes a screw that engages female threads (not shown) in an opening of cover 206, allowing the pressure of the sensor 204 on the chest wall 202 to be adjusted. It is contemplated that the adjusting means 208 may include a spring having a suitable spring constant for automatically adjusting the pressure of the sensor 204 on chest wall 202 to maintain a suitable coupling. It is understood that any adjusting means capable of providing suitable coupling of the sensor 204 to the chest wall 202 to ensure accurate transmission of heart sounds from the chest wall 202 to the sensor 204 may be used.

Although FIG. 2A shows adjusting means 208 extending through the cover 206, it is contemplated that the adjusting means may be placed within cover 206 if adjustment of the sensor coupling is not used, for example, if a spring is used to apply the coupling force. A gel (not shown) may be provided between the sensor 204 and chest wall 202 in order to increase heart sound transmission to the sensor 204. A cable (not shown) may be provided to connect sensor 204 to signal conditioner 106.

PCG sensor 104 may further include a holding means 210 for coupling the cover 206 to the chest wall 202. In an exemplary embodiment, the holding means 210 includes an adhesive belt for securing the cover, and, thus the sensor 204, to the chest wall 202 by wrapping the belt around the patient and over the cover 206. It is contemplated that the holding means 210 may include any means to secure the cover 206 to chest wall 202 while permitting adjustment of the sensor 204 using adjusting means 208. For example, holding means 210 may include an adhesive tape attached between the chest wall 202 and the cover 206. It is further contemplated that the lip of cover 206 that is coupled to the chest wall 202 may include an adhesive material to form the holding means 206. It is also contemplated that the holding means 210 may include a vacuum system to secure the cover 206 to chest wall 202. A vacuum system may further inhibit the transmission of background noise to the sensor 204.

Figure 2B:
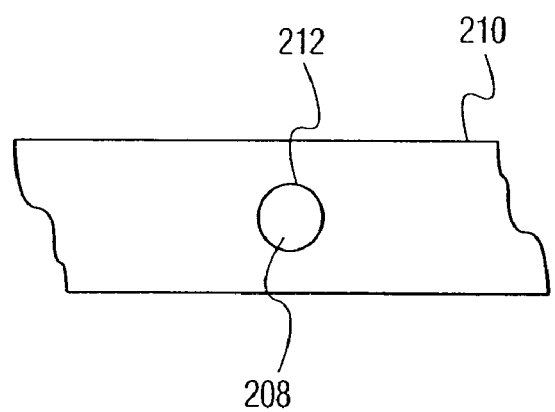
FIG. 2B is an overhead plan drawing illustrating an exemplary holding means shown in FIG. 2A, according to an embodiment of the present invention.

FIG. 2B is an overhead plan drawing illustrating an exemplary holding means 210 shown in FIG. 2A, according to an embodiment of the present invention. Holding means 210 may include an aperture 212 for receiving adjusting means 208 so that holding means 210 may be directly coupled to the cover 206. In this manner, the cover 206 may be secured to the chest wall 202 free of movement along the chest wall 202.

The exemplary PCG sensor 104 shown in FIG. 2A desirably increases the transmission of heart sounds to sensor 204 through the use of the adjusting means 208 and holding means 210, for example, by reducing any attenuation and/or distortion effects provided by the underlying tissue. In addition, the cover 206 may attenuate background noise to sensor 204.

Figure 3A:
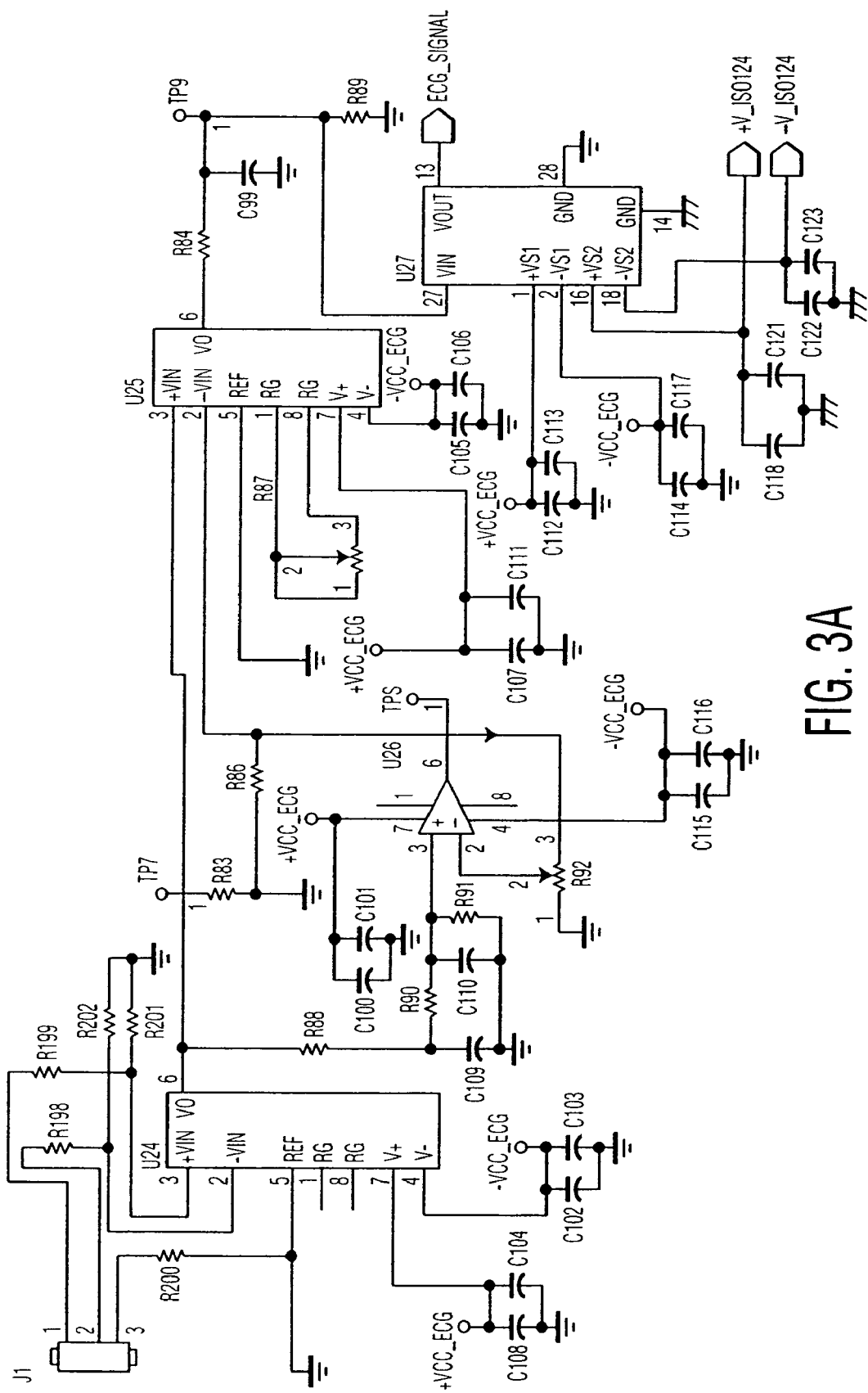
FIG. 3A is a circuit diagram illustrating an exemplary electrocardiogram (ECG) signal conditioner shown in FIG. 1A, according to an embodiment of the present invention.

FIG. 3A is a circuit diagram illustrating an exemplary ECG signal conditioner 105 shown in FIG. 1A, according to an embodiment of the present invention. Table 1 provides circuit components and component values, according to an exemplary embodiment of the present invention. The ECG signal conditioner 105 includes a differential amplifier that amplifies one or more differential voltages among or between the multiple ECG electrodes. The conditioned analog ECG signal is provided to the connection module 132 of data acquisition system 108.

TABLE 1

| ECG Signal Conditioner Circuit Values | |
|---|---|
| R202 | 1200 Ω |
| R201 | 4500 Ω |
| R84 | 12 kΩ |

TABLE 1-continued

ECG Signal Conditioner Circuit Values

| R87 | 20 kΩ |
|---|---|
| R200 | 22 kΩ |
| R83, R86, R198, R199 | 33 kΩ |
| R92 | 50 kΩ |
| R89 | 82 kΩ |
| R88, R90, R91 | 560 kΩ |
| C99, C101, C103, C104, C106, C111, C113, C116, C117, C121, C123 | 100 nF |
| C100, C102, C105, C107, C108, C112, C114, C115, C118, C122 | 1 µF |
| C109, C110 | 4.7 µF |
| U24 (Gain of 5 Instrumentation Amplifier) | AD8225 |
| U25 (Low Power Instrumentation Amplifier) | INA128 |
| U26 (Operational Amplifier) | OP27 |
| U27 (Isolation Amplifier) | ISO124/SO |
| J1 (Connector) | 3-Pin |

Figure 3B:
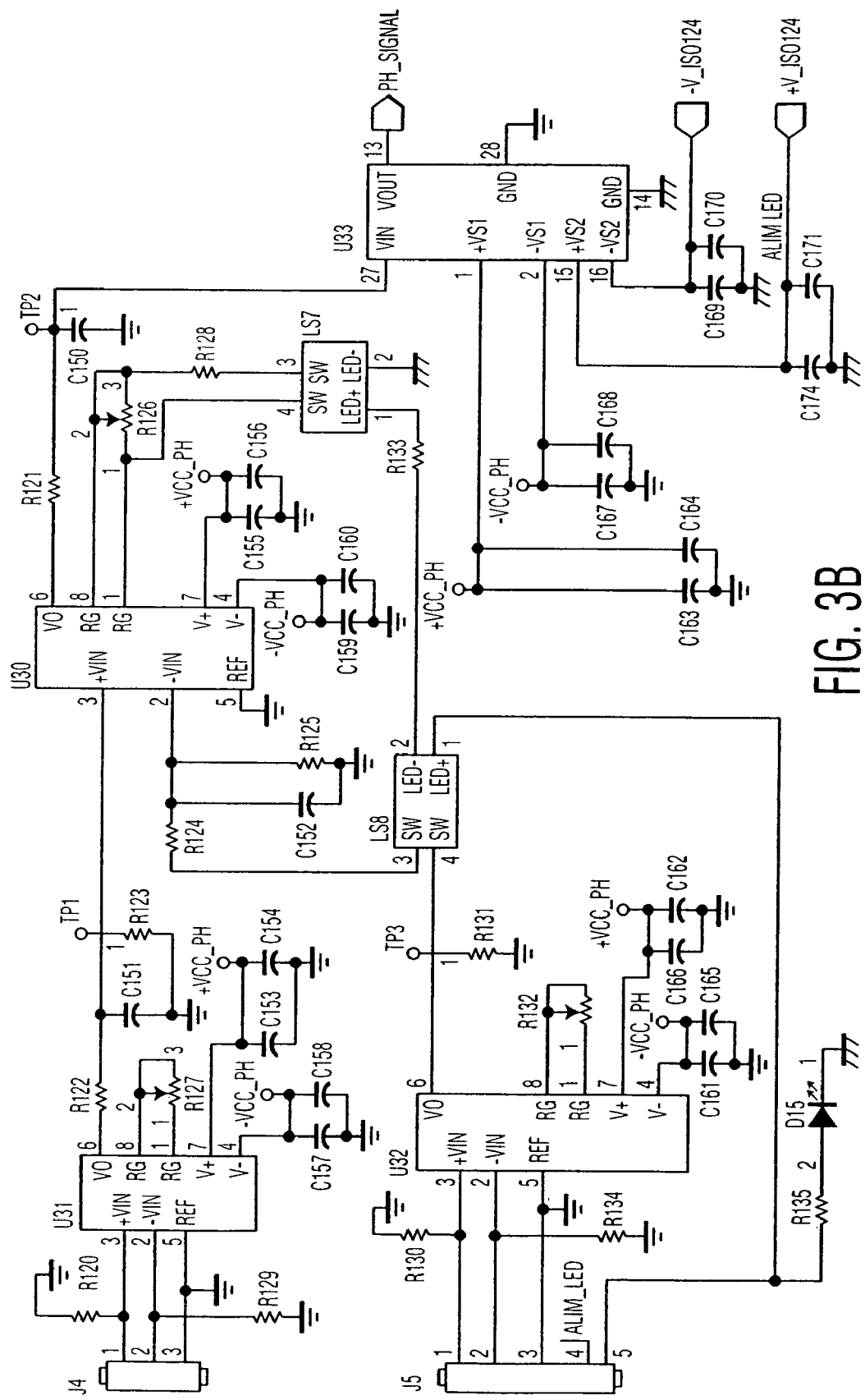
FIG. 3B is a circuit diagram illustrating an exemplary PCG signal conditioner shown in FIG. 1A, according to an embodiment of the present invention.

FIG. 3B is a circuit diagram illustrating an exemplary PCG signal conditioner 106 shown in FIG. 1A, according to an embodiment of the present invention. Table 2 provides circuit components and component values, according to an exemplary embodiment of the present invention. Although FIG. 1A illustrates a single PCG sensor 104, in an exemplary embodiment two PCG sensors 104 may be provided to PCG signal conditioning circuit 106, as shown in FIG. 3B. Each of the PCG sensors 104 is desirably the same model number having substantially identical frequency and sensitivity characteristics. Each of the PCG sensors is desirably configured as described above with respect to FIG. 2A such that each sensor 204 is placed in separate covers 206 (FIG. 2A) and separately attached to the chest wall. The first PCG sensor 104 is desirably placed on the chest wall at a location for maximum heart sound transmission. The second PCG sensor 104 is desirably placed close to the first PCG sensor 104 but in a position in which the heart sounds are substantially attenuated with respect to the first PCG sensor 104.

The PCG signal conditioner 106 may include a noise reduction circuit to determine a difference between the first and second PCG sensors 104 and, thus, reduce any background noise common to both PCG sensors 104. Common background noise may include, for example, blood flow or breathing noise.

In an exemplary embodiment, the PCG signal conditioner 106 includes a band-pass filter that passes frequencies within a range of about 15 Hz to 550 Hz, and, in particular, in a range of 20-550 Hz. In an exemplary embodiment, the PCG signal conditioner 106 uses a filter that approximates a rectangular window filter in order to suppress components outside of the typical frequency range of the PCG signal.

The PCG signal conditioner 106 of PCG sensor 104 may amplify the PCG signal and provide an impedance matching function to match an impedance of PCG sensor 104 to data acquisition system 108. The PCG signal conditioner may further include a gain control circuit that adjusts the gain of the PCG signal based on whether the DAQ/analysis controller 134 determines that the digitized PCG signal is saturated.

TABLE 2

PCG Signal Conditioner Circuit Values

| R128 | 820 Ω |
|---|---|
| R135 | 1200 Ω |
| R133 | 2.2 kΩ |
| R121, R122, R124 | 4.7 kΩ |
| R126, R127, R132 | 20 kΩ |
| R123, R125 | 33 kΩ |
| R120, R129, R130, R134 | 47 kΩ |
| R131 | 100 kΩ |
| C150, C151, C152 | 10 nF |
| C154, C156, C158, C160, C162, C164, C165, C168, C170, C171 | 100 nF |
| C153, C155, C157, C159, C161, C163, C166, C167, C169, C174 | 1 µF |
| U30, U31, U32 (Low Power Instrumentation Amplifier) | INA128 |
| D15 | LED |
| J4 (Connector) | 3-Pin |
| J5 (Connector) | 5-Pin |
| LS7, LS8 (PhotoMOS Relay) | AQY210 |
| U33 (Isolation Amplifier) | ISO124/SO |

A suitable ECG sensor 102, PCG sensor 104, signal conditioner 106, data acquisition system 108, PAP analyzer 110, storage means 126, storage means 131, display 128 and control interface 130 for use with the present invention will be understood by one of skill in the art from the description herein.

The exemplary apparatus 100 may provide a noninvasive method for estimating the PAP that is easy to use by physicians, nurses, technicians, paramedics, researchers or any one of skill in the art. A user may be easily trained to use the apparatus in a relatively short time period. For example, the apparatus 100 may not require significant set up time and may be configured to acquire data and estimate the PAP for frequent and/or continuous monitoring of a patient without discomfort for the patient. The exemplary apparatus 100 reliably and consistently yields real time values of PAP, for example, for the diagnosis, evaluation, and monitoring of pulmonary artery hypertension estimated, noninvasively, from the analysis of the S2 recorded with a PCG sensor. Health related personnel can be quickly trained to manage the exemplary apparatus 100 in different patient settings, including noisy environments.

The exemplary apparatus 100 may be used as a desktop or handheld instrument. The apparatus 100 may be implemented on different types and sizes of computers as well as computers having different processing power capabilities. Hardware upgrades and/or software upgrades, for example algorithm modifications, may be provided. The analyzed data may be reviewed off-line for research purposes and/or further evaluation of patient data.

The exemplary apparatus 100 may also provide a signal acquisition and thus analysis that is not significantly affected by environmental noise and/or noise provided by other devices present, for example, a mechanical respirator or an aortic pump.

Figure 4:
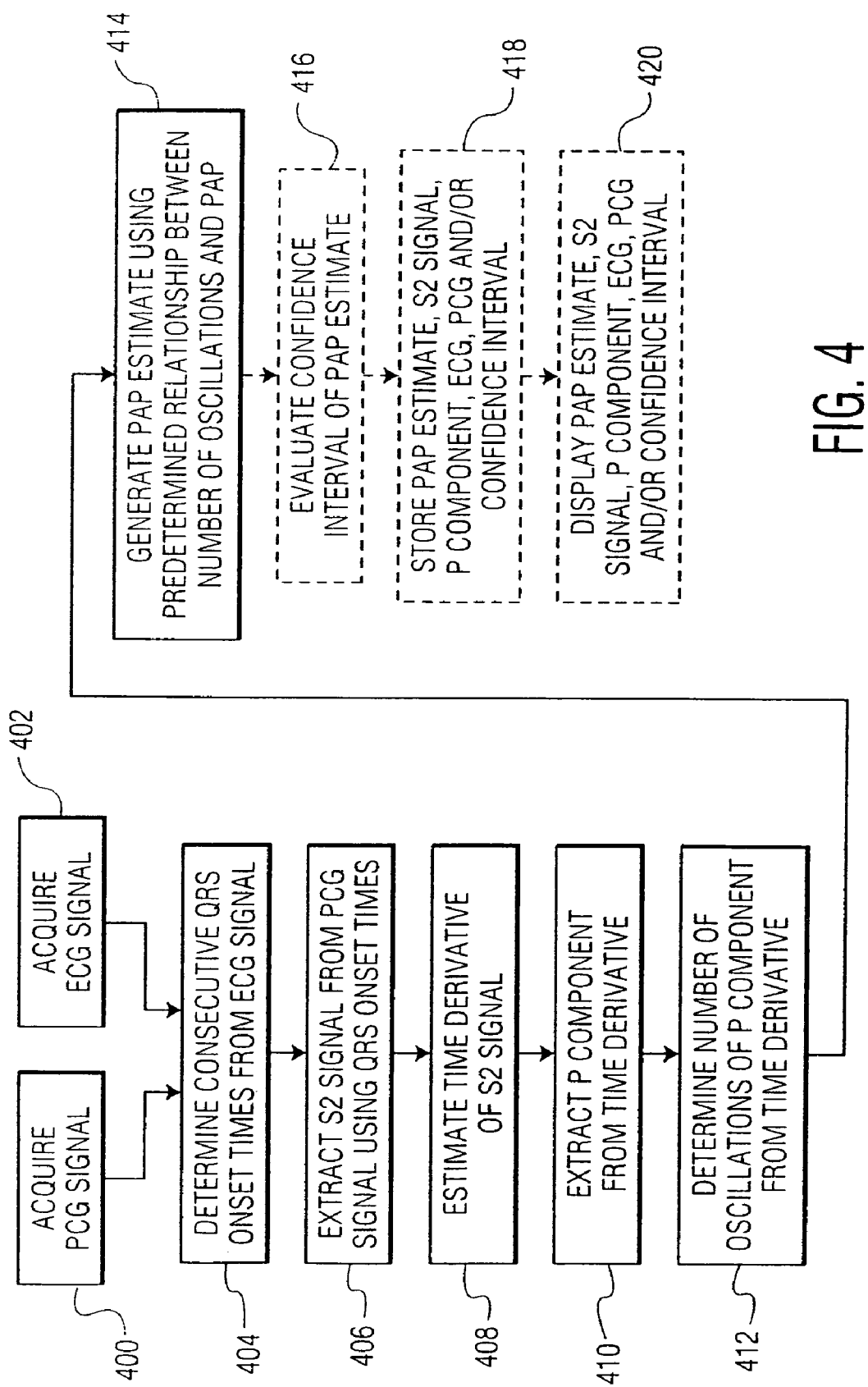
FIG. 4 is a flowchart illustrating an exemplary method for noninvasively estimating PAP according to an embodiment of the present invention.
Figure 5:
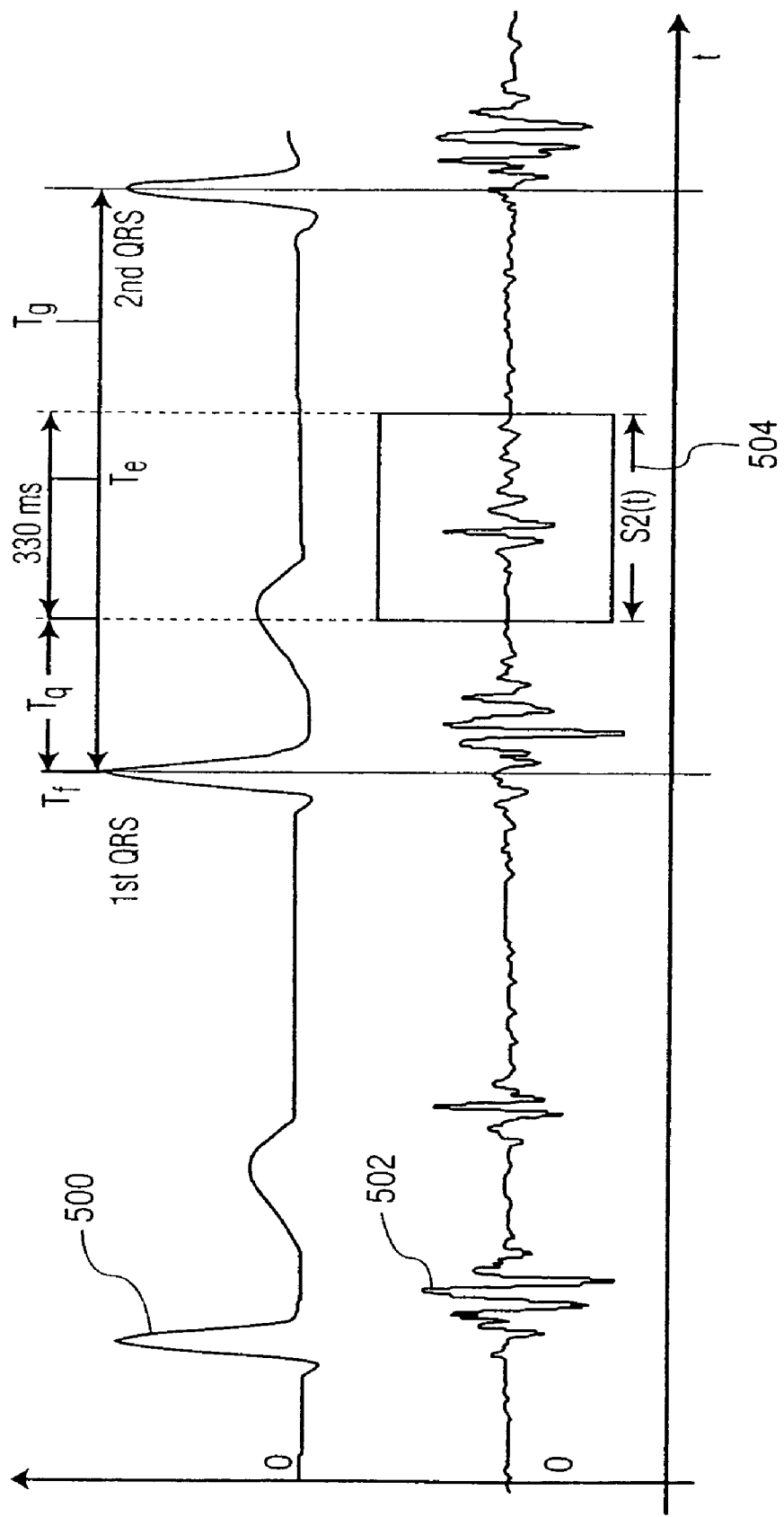
FIG. 5 is a graph of signal amplitude versus time that is useful for illustrating extraction of a second heart sound (S2) signal from a PCG signal according to the exemplary method shown in FIG. 4.
Figure 6:
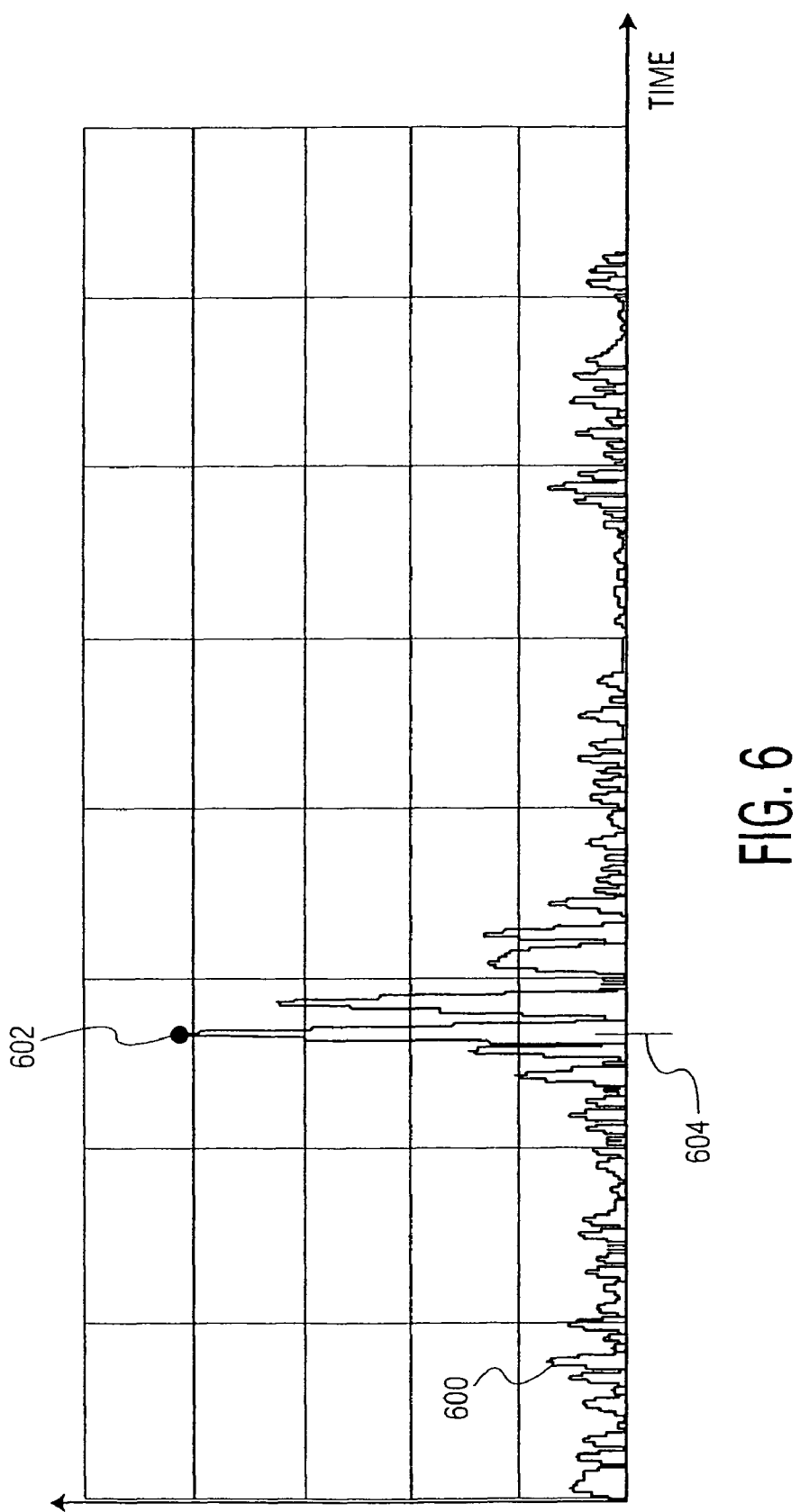
FIG. 6 is a graph of signal magnitude versus time that is useful for illustrating extraction of a pulmonary (P) component of the S2 signal according to the exemplary method shown in FIG. 4.
Figure 7:
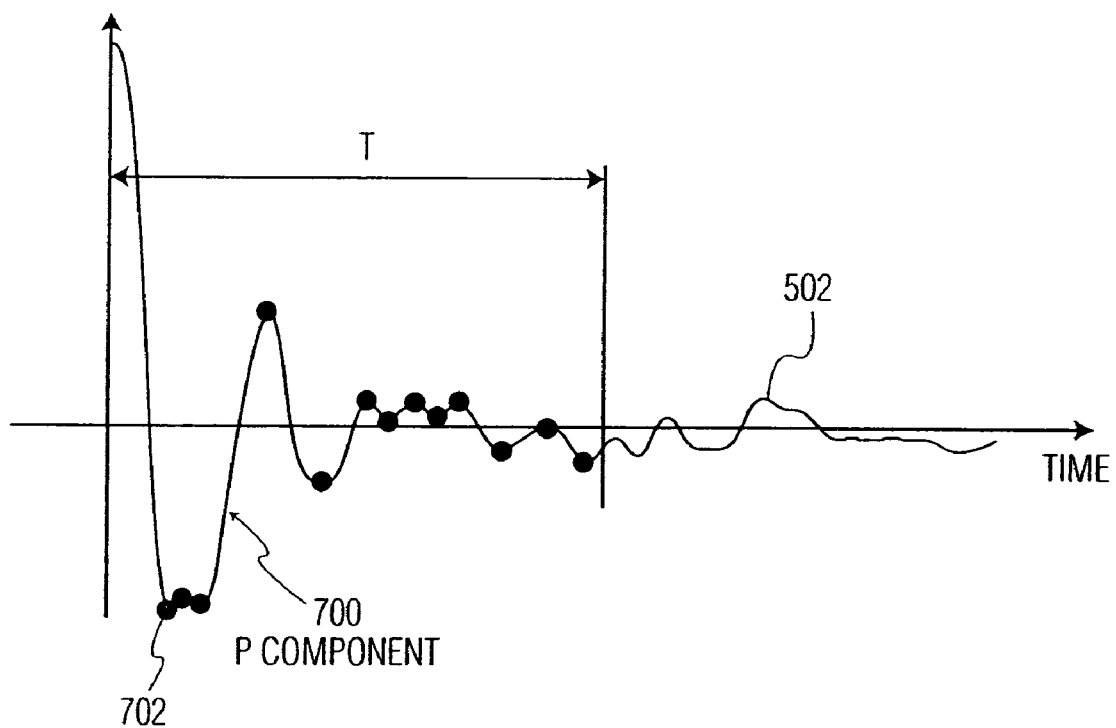
FIG. 7 is a graph of signal amplitude versus time that is useful for illustrating determination of a number of oscillations of the P component according to the exemplary method shown in FIG. 4.

FIG. 4 is a flowchart illustrating an exemplary method for noninvasively estimating the PAP according to an embodiment of the present invention. The following figures illustrate examples of the exemplary method shown in FIG. 4: FIG. 5 is an exemplary S2 signal extracted from the PCG signal; FIG. 6 is an exemplary P component extracted from the S2 signal; and FIG. 7 is an example illustrating determination of a number of oscillations of the P component.

Referring to FIG. 4, in step 400, a PCG signal is acquired and in step 402 an ECG signal is acquired. The PCG signal and ECG signal are desirably synchronously acquired, for example, using data acquisition system 108 with ECG sensor 102 and PCG sensor 104 (FIG. 1).

In step 404, two consecutive QRS complex onset times are determined using known in the art techniques from the ECG signal. In an exemplary embodiment, the first two consecutive QRS complex onset times are used to extract the S2 signal. It is understood that any pair of QRS complex onset times may be used to extract the S2 signal. The QRS complex onset times may be used to define an interval containing an S2 signal within the PCG signal. Referring to FIG. 5, a first QRS complex onset time, $T_f$, and a second QRS complex onset time, $T_g$, are determined from ECG signal 500.

In step 406, an S2 signal 504 is extracted from the PCG signal 502 using the determined QRS complex onset times $T_f$ and $T_g$. As shown in FIG. 5, a time interval, $T_e$, may be calculated from the two QRS complex onset times. An S2 onset time for the S2 signal 504 may be determined according to the calculated time interval. In an exemplary embodiment, a time interval, $T_q$, corresponding to a quarter of time interval $T_e$ may be used as the S2 onset time.

A predetermined portion of the PCG signal 502 beginning with the S2 onset time is extracted as the S2 signal 504. In an exemplary embodiment, the predetermined portion corresponds to 330 ms. The inventors have determined that an S2 signal is included within a 330 ms portion of the PCG signal 502 having an S2 onset time corresponding to $T_q$. It is contemplated that any suitable portion of the PCG signal 502 that includes the P component of the S2 signal may be used in order to extract an S2 signal. The extracted S2 signal may further be normalized. Steps 404 and 406 may be performed by S2 extractor 112 (FIG. 1A).

Referring back to FIG. 4, in step 408, a time derivative of the extracted S2 signal (herein time derivative signal) is estimated, for example using time derivative estimator 116 (FIG. 1A). In an exemplary embodiment, a first order time derivative signal is estimated in order detect the onset of the P component and to calculate a number of oscillation in the P component based on a change in sign of the first order time derivative. It is contemplated that any of a number of well known numerical methods may be used to estimate the time derivative and that a higher order time derivative may be estimated in order to perform one or more of P component detection and calculation of a number of oscillations of the P component.

In an exemplary embodiment, the first order time derivative signal is estimated according to eq. (1) as:

$$d(i)=[s(i+1)-s(i)]\cdot f_s \quad (1)$$

where d(i) represents the first order time derivative signal, i represents a sample index and $f_s$ represents the sampling rate. The inventors have determined that in a region of separation of an A and the P component of the S2 signal, a value of d(i), in absolute value, increases, both if the A and P components are separated and also if they are overlapped, thus the P component may be determined whether or not the A and P component are separated.

In step 410, the P component is extracted from the time derivative signal, for example, using P component extractor 118 (FIG. 1A). Referring to FIG. 6, a maximum absolute value 602 of the time derivative signal 600 is determined. A time index, $i_p$, corresponding to the maximum absolute value 602 forms the P component onset time 604. A predetermined portion of the time derivative signal 600 is selected using the P component onset time 604 in order to form the extracted P component. Although in an exemplary embodiment, the predetermined portion is 113.3 ms, it is contemplated that any portion that includes a suitable number of P component oscillations (i.e. P component energy) may be used to extract the P component. It is understood that a duration of the P component may vary by individual and that the predetermined portion may be determined by an average duration over a number of individuals.

Referring back to FIG. 4, in step 412 a number of oscillations of the P component is determined from the time derivative signal, for example using P component oscillation calculator 120 (FIG. 1A). Referring to FIG. 7, a portion of PCG signal 502 having the P component 700 is shown where T represents a predetermined duration (i.e. predetermined portion) of the P component of the extracted S2 signal. The P component includes a number of oscillations represented generally by points 702. The number of oscillations is related to various vibration modes and is directly related to the highest frequency components of the P component. According to the exemplary method of the present invention, a fundamental vibration mode and an overall contribution of higher-order vibration modes in the time domain are desirably used by counting the number of oscillations that occur in the predetermined time interval T. By using the higher-order vibration modes in addition to the fundamental vibration mode, a right shift (i.e. a shift toward higher frequencies) of the spectral. bandwidth as well as an enlargement of the spectral bandwidth (due to the contribution of the higher-order vibration modes) may be taken into account.

According to an exemplary method, the number of oscillations is determined based on a corresponding number of times that the P component of the first time derivative signal inverts its sign. It is known to one of skill in the art that the first time derivative illustrates a trend in an angular coefficient of a line tangent to a signal at each time instant so that a change in sign of the first time derivative corresponds to the location where a signal reaches its maximum or minimum.

In this context, for the extraction of the P component, the following mode of operation may be provided: 1) an S2 signal may be extracted from the PCG signal, 2) an absolute value of a time derivative of the S2 signal may be evaluated, 3) a time instant corresponding to a beginning of the time derivative may be assumed to be zero, 4) a maximum of the absolute value of the time derivative representing the P component onset time may be determined and 5) a P component having a predetermined duration may then be extracted using the onset time and the predetermined duration.

Referring back to FIG. 4, in step 414, a PAP estimate is generated using a predetermined relationship between the number of oscillations and PAP, for example with PAP estimator 122 (FIG. 1A). In an exemplary embodiment, the predetermined relationship is given by eq. (2) as:

$$PAP\ Estimate = 22\cdot\left(2^{\left(\frac{N}{6}\right)} - 2\right)\ mmHg \quad (2)$$

where N represents the number of oscillations determined in step 412. In general, the relationship can be presented as given by equation (3) as:

$$PAP\ Estimate = a1\cdot\left(a2^{\left(\frac{N}{a3}\right)} + a4\right)\ mmHg \quad (3)$$

where parameters a1, a2, a3 and a4, b, d can be determined experimentally, for example, as described below.

In an exemplary embodiment, the predetermined relationship shown in eq. (2) is determined through known in the art linear regression techniques based on PAP measurements obtained using a right-sided cardiac catheterization technique as well a number of oscillations measured using the exemplary system 100 (FIG. 1A). A large number of measurements were collected from each patient in order to evaluate a measurement interval for each PAP measurement (i.e. via the catheterization technique). This procedure is in accordance with the NF ENV 13005 standard "ISO Guide to the Expression to the Uncertainty in Measurement," Geneva, Switzerland, 1995, which prescribes the evaluation of the statistical mean value and of the standard uncertainty of a measurement gauged by means of experimental results. According to the exemplary embodiment, the standard uncertainty is given by kS, where k is the coverage factor and S is the estimate of the standard deviation σ associated to the expected value:

$$S = \sqrt{\frac{1}{N}\sum_{n=1}^{N}(PAP_n - \mu)^2} \quad (4)$$

where $PAP_N$ the generic $n^{th}$ PAP evaluated and $\mu$ the estimate of the mode of the entire set of PAPs.

In step 416, a confidence interval measure of the PAP estimate is evaluated, for example, using confidence interval evaluator 124 (FIG. 1). The confidence interval measure may be evaluated for a predetermined number of PCG and corresponding ECG signals. In an exemplary embodiment, the confidence interval measure represents a 95% confidence interval for the PAP estimate. In this embodiment, for a predetermined number of acquired PCG and ECG signals, a standard uncertainty is determined as described above.

If a plurality of PAP estimates are generated, a frequency density of the PAP estimates may be determined. An interval corresponding to the 95% confidence interval around the mode of the frequency density may be used as the confidence interval measure. The frequency density may be determined by considering an interval delimited by the maximum and minimum values of the PAP estimates and subdividing the interval into equally spaced subintervals. In an exemplary embodiment, the subintervals are in the range of 3-5 mmHg and, in particular, approximately 4 mmHg. A frequency distribution in the subintervals may be computed and a mode PAP estimate determined. An interval of the PAP estimates may be given by the lower and higher PAP estimates of the confidence interval corresponding to the found mode PAP estimate.

In alternate step 418, one or more of the PCG signal, the ECG signal, the extracted S2 signal, the P component, the PAP estimate and the confidence interval measure may be stored, for example in storage means 126. In alternate step 420, one or more of the PCG signal, the ECG signal, the extracted S2 signal, the P component, the PAP estimate and the confidence interval measure may be displayed, for example on display 128.

Figure 8:
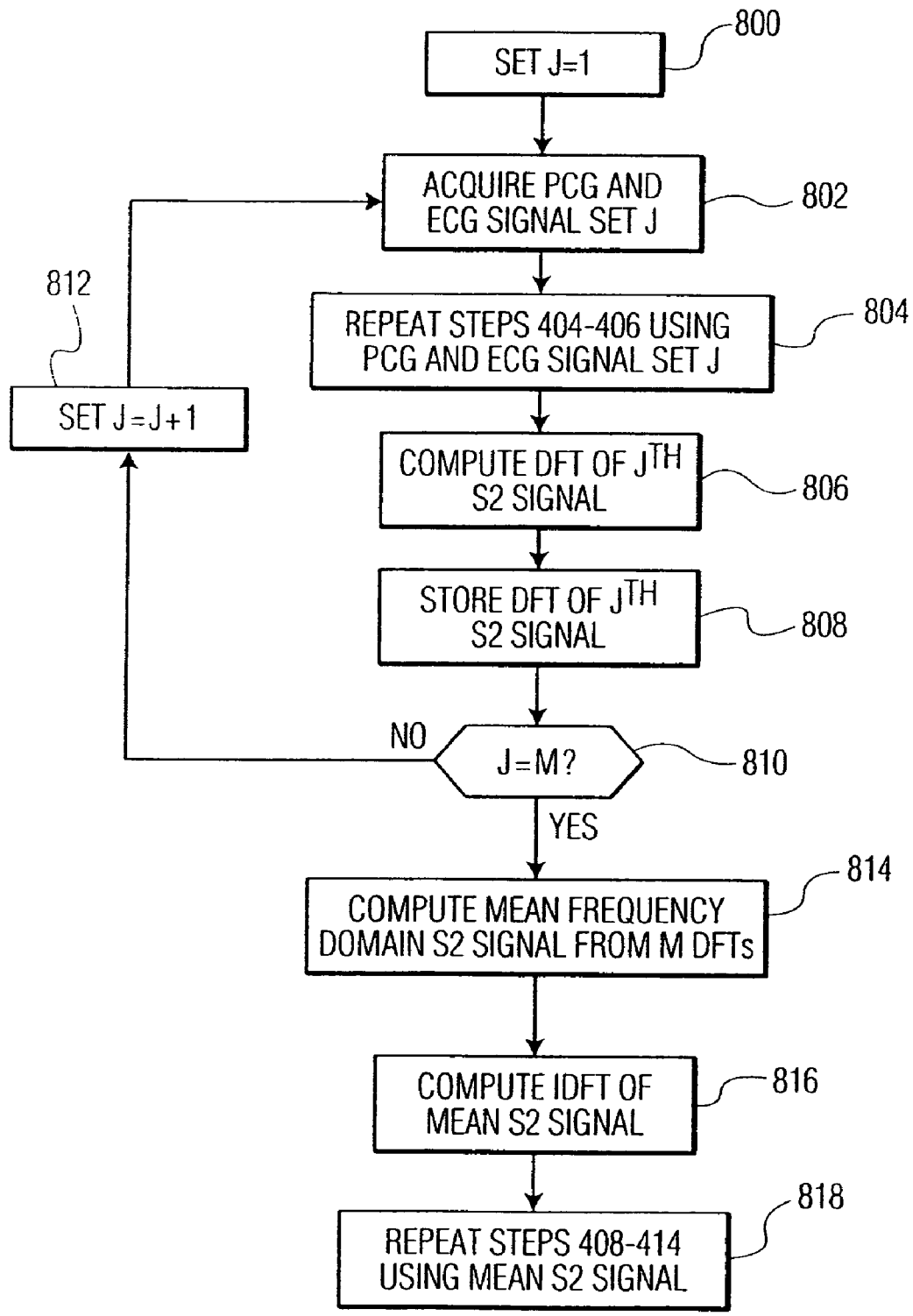
FIG. 8 is a flowchart illustrating an exemplary method for generating a PAP estimate using a plurality of acquired PCG and electrocardiogram (ECG) signals, according to an embodiment of the present invention.
Figure 9:
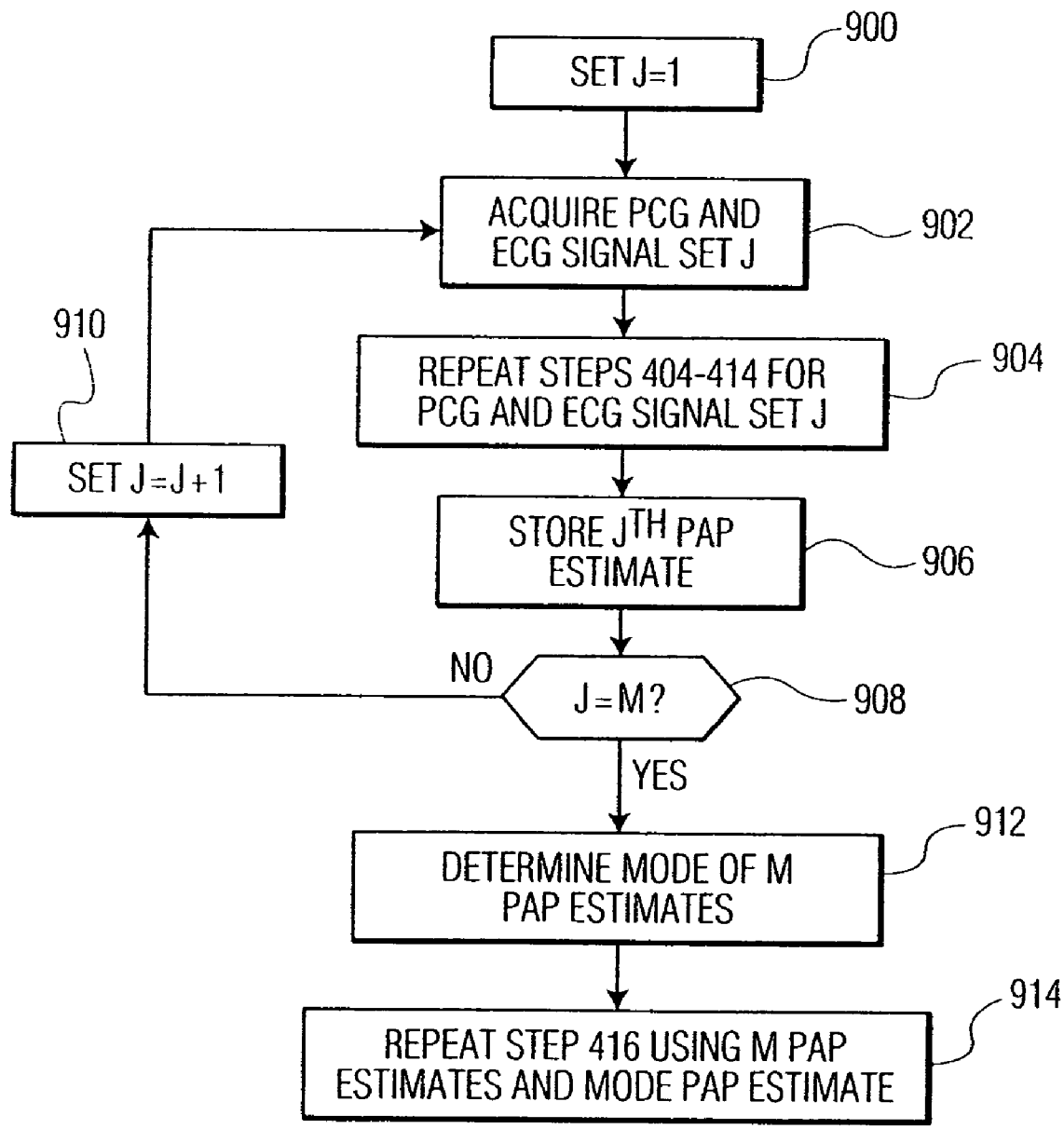
FIG. 9 is a flow chart illustrating an exemplary method for generating a PAP estimate using a plurality of acquired PCG and ECG signals, according to a further embodiment of the present invention.

As described above, a predetermined number of PCG signals and corresponding ECG signals may be acquired and a PAP estimate may be determined from the plurality of acquired sets of signals. Referring now to FIGS. 8 and 9 alternate exemplary embodiments are illustrated for generating a PAP estimate from the plurality of acquired sets of signals.

FIG. 8 is a flowchart illustrating an exemplary method for generating a PAP estimate using a predetermined number of acquired PCG and ECG signals, according to an embodiment of the present invention. In step 800, a variable J is initialized. The variable J represents a $J^{th}$ signal set of the predetermined number, M, of PCG and corresponding ECG signals to be acquired. In step 802, PCG and ECG signal set J are synchronously acquired, for example using data acquisition system 108 (FIG. 1A). In step 804, steps 404-406 (FIG. 4) are repeated using PCG and ECG signal set J in order to extract the $J^{th}$ S2 signal corresponding to signal set J.

In step 806, a DFT signal of the $J^{th}$ extracted S2 signal is computed, for example using DFT processor 138 (FIG. 1C). In step 808, the DFT signal of the $J^{th}$ S2 signal, (herein DFT(J)), is stored, for example, in storage means 131 (FIG. 1A).

In step 810, it is determined whether the predetermined number M of signal sets have been acquired and processed. If fewer than M signal sets have been acquired, step 810 proceeds to step 812 to update the signal set variable J and steps 802-810 are repeated.

If the predetermined number M of signal sets have been acquired and processed, step 810 proceeds to step 814. In step 814, a mean frequency-domain S2 signal is computed from the M DFT signals. For example, the stored DFT signals may be provided to mean calculator 140 (FIG. 1C). In step 816, an IDFT signal of the frequency-domain S2 is computed, for example using IDFT processor 142 (FIG. 1C) to form the time-domain mean S2 signal.

In step 818, steps 408-414 are repeated using the time-domain mean S2 signal in order to generate a PAP estimate. It is contemplated that any of steps 418-420 may be repeated to store or display desired values and signals.

FIG. 9 is a flow chart illustrating an exemplary method for generating a PAP estimate using a plurality of acquired PCG and ECG signals, according to a further embodiment of the present invention. In step 900, a variable J is initialized. The variable J represents a $J^{th}$ signal set of the predetermined number, M, of PCG and corresponding ECG signals to be acquired. In step 902, PCG and ECG signal set J are synchronously acquired, for example using data acquisition system 108 (FIG. 1A). In step 904, steps 404-414 (FIG. 4) are repeated using PCG and ECG signal set J in order to generate a $J^{th}$ PAP estimate corresponding to signal set J. In step 906, the $J^{th}$ PAP estimate is stored, for example using storage means 131 (FIG. 1A).

In step 908, it is determined whether the predetermined number M of signal sets have been acquired and processed. If fewer than M signal sets have been acquired, step 908 proceeds to step 910 to update the signal set variable J and steps 902-908 are repeated.

If the predetermined number M of signal sets have been acquired and processed, step 908 proceeds to step 912. In step 912, a mode PAP estimate is determined from the M stored PAP estimates. In step 914, step 416 is repeated to determine a confidence interval measure using the mode determined in step 912 and the M PAP estimates, using a frequency density as described above. It is contemplated that any of steps 418-420 may be repeated to store or display desired values and signals.

Figure 10:
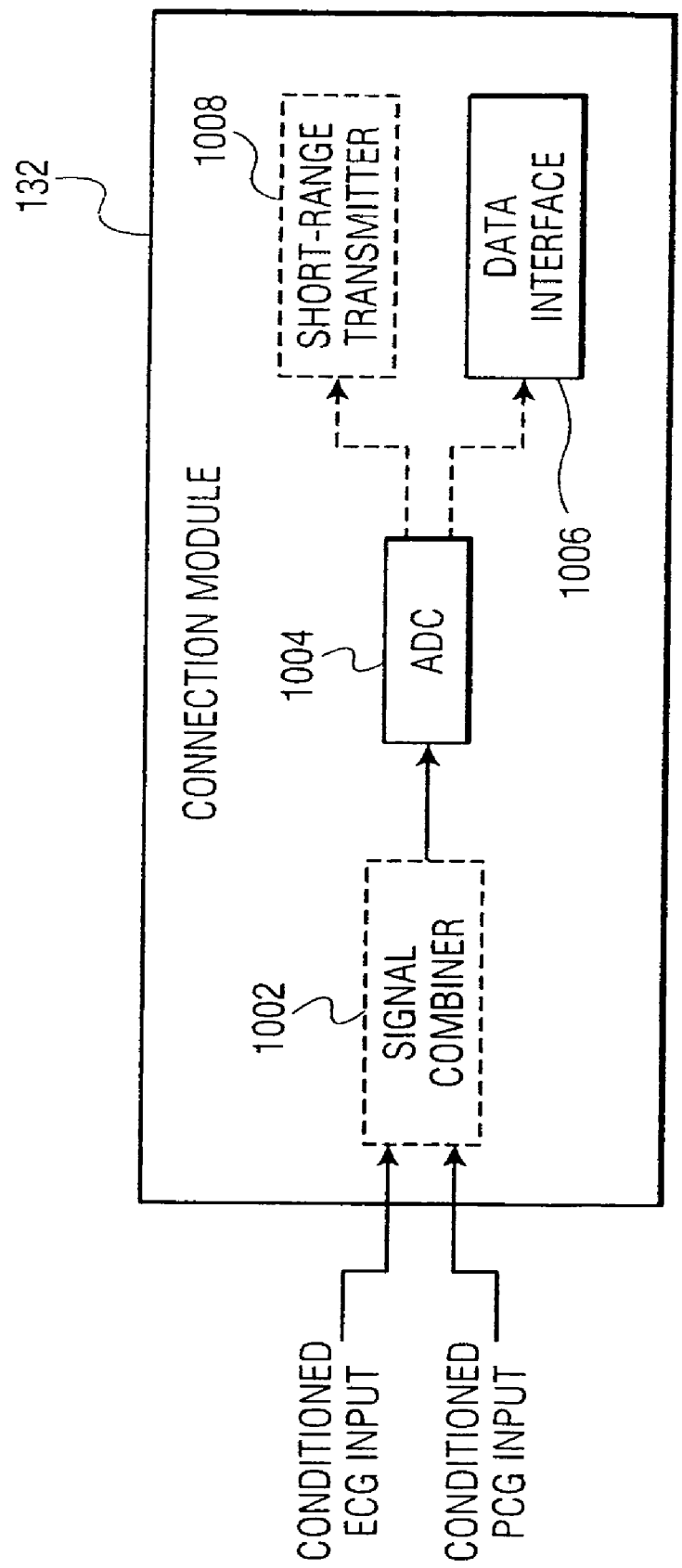
FIG. 10 is a functional block diagram illustrating an exemplary connection module shown in FIG. 1B, according to an embodiment of the present invention.

As described above, a system and methods are presented for determining a PAP estimate from one or more sets of ECG and corresponding PCG signals. Referring now to FIGS. 10 and 11, an exemplary connection module having an optional short-range connection and a method for acquiring data using the exemplary connection module are described below.

FIG. 10 is a functional block diagram illustrating an exemplary connection module 132 generally described with respect to FIG. 1B. In an exemplary embodiment, connection module 132 receives the conditioned ECG and PCG signals from respective ECG signal conditioner 105 and PCG signal conditioner 106 and converts the analog signals to digital signals with an ADC 1004. The digitized signals may be transmitted to the DAQ/analysis controller 134 (FIG. 1B) using data interface 1006. In an exemplary embodiment, data interface 1006 includes a universal serial bus (USB) port capable of transmitting the digitized ECG and PCG signals separately using a stereo audio compression/decompression (codec) interface.

Optionally, the digitized signals may be transmitted to the DAQ/analysis controller 134 (FIG. 1B) using short-range transmitter 1008, such as a Bluetooth transmitter such that the DAQ/analysis controller 134 (FIG. 1B) includes a short-range transceiver (not shown) capable of receiving the digitized PCG and ECG signals via a short-range connection. In an exemplary embodiment, the short-range transmitter 1008 includes a Free2move F2M03Ac2-HP Bluetooth module and is capable of transmitting a single signal using a mono codec interface. Because the short-range transmitter may transmit a single signal, the conditioned ECG and PCG signals are combined using signal combiner 1002 prior to digitization by ADC 1004.

In an exemplary embodiment, signal combiner 1002 applies a frequency modulation (FM) scheme to the conditioned ECG signal using an FM modulator (not shown). This FM modulated ECG signal is combined with the conditioned PCG signal, for example with a summation circuit, and provided to the ADC 1004. Although an FM modulation scheme is illustrated, it is contemplated that any suitable method may be used to combine the conditioned ECG and PCG signals that maintains the desirable signal characteristics of each signal. It is contemplated that either the DAQ/analysis controller 134 (FIG. 1B) or the PAP analyzer 110 (FIG. 1A) may include an FM demodulator to demodulate the ECG signal from the single signal transmitted from the short-range transmitter 1008. Although in an exemplary embodiment the FM modulation is provided at a frequency in a range between 1.6 kHz to 3.6 kHz, it is contemplated that any desirable FM frequency may be used.

FIG. 11 is a flow chart illustrating an exemplary method for performing data acquisition by the DAQ/analysis controller 134 (FIG. 1B), according to an embodiment of the present invention where the connection module 132 includes short-range transmitter 1008 (FIG. 10) and DAQ/analysis controller 134 (FIG. 1B) includes a short-range transceiver (not shown). In step 1100, an instruction is received to perform data acquisition. In an exemplary embodiment, control interface 130 (FIG. 1A) includes a push button for generating the data acquisition instruction and provides the instruction to DAQ/analysis controller 134 (FIG. 1B). In step 1102, the DAQ/analysis controller 134 acknowledges receipt of the data acquisition instruction by providing a display status on display 128 (FIG. 1A). In an exemplary embodiment, this display status includes configuring an LED to emit a green color.

In step 1104, the DAQ/analysis controller 134 checks for establishment of a short-range connection between the DAQ/analysis controller 134 and the connection module 132 within a predetermined time. Although in an exemplary embodiment this time period is two minutes, it is understood that this predetermined time may include any desirable communication establishment time. In an exemplary embodiment, the connection module 132 is configured to power off after two minutes in order to conserve battery power. In an exemplary embodiment, the predetermined time corresponds to the time period in which the connection module 132 is powered on.

In step 1106 it is determined whether a connection is established within the predetermined time. If the connection is not established, step 1106 proceeds to step 1108 and the connection module 132 is shut down, i.e. powered off.

If the connection is established, step 1106 proceeds to step 1110. In step 1110, the DAQ/analysis controller 134 acknowledges the connection by configuring the display 128 (FIG. 1A) to change its display status. In an exemplary embodiment, an LED displays a blinking blue color.

In step 1112, the DAQ/analysis controller 134 transmits a start-acquisition command to connection module 132. In an exemplary embodiment, the connection module 132 includes a counter (not shown) that is used to count down to a time for powering off the connection module 132. The start-acquisition command from the DAQ/analysis controller 134 is used to reset the clock in order to maintain its powered on status. In step 1114, it is determined whether the start-acquisition command is transmitted within the predetermined time, i.e. prior to shut down of the connection module 132. If the command is not transmitted within the predetermined time, step 1114 proceeds to step 1108 and the connection module is shut down, i.e. powered off.

If the command is transmitted within the predetermined time, step 1114 proceeds to step 1116. In step 1116, the acquired data is retrieved by the DAQ/analysis controller 134 from the connection module 132.

In step 1118, a status of the short-range connection is checked by the DAQ/analysis controller 134. Although step 1118 is illustrated as occurring in sequential order with step 1116, it is contemplated that step 1118 may occur throughout the acquisition process. In step 1120, it is determined whether a suitable short-range connection is provided.

If the connection fails, step 1120 proceeds to step 1122 and the DAQ/analysis controller 134 configures the display 128 to alert the user to the failed connection. In an exemplary embodiment, the display 128 includes an audio output such that both an LED is configured to emit a red color and a buzzer produces an audible output. It is contemplated that any suitable display and/or audio output may be provided to alert a user to a failed connection. In step 1124, the DAQ/analysis controller 134 retries establishing a connection with the connection module 132. In step 1126, the process is repeated from step 1104.

If the connection is maintained, step 1120 proceeds to step 1128. In step 1128, it is determined whether all of the data is acquired. For example, the control interface 130 (FIG. 1A) may select a number of ECG and PCG signal sets to be acquired for PAP analysis, such as by the method illustrated in FIG. 8, and provide this number of signal sets to the DAQ/analysis controller 134. If all of the data is not acquired, step 1128 proceeds to step 1130. In step 1130, the process is repeated from step 1112.

If all of the data is acquired, step 1128 proceeds to step 1132, and the acquisition is complete. In an exemplary embodiment, because the connection module 132 includes a counter (not shown) to automatically shut down, further action by the user via control interface 130 may not be needed to shut down the connection module 132.

Although not illustrated in FIG. 11, an exemplary embodiment of the present invention includes capability by the DAQ/analysis controller 134 to determine and alert a user (such as via display 128 (FIG. 1A) of a low battery condition, such as for connection module 132 (FIG. 1B). In an exemplary embodiment, if the battery charge becomes low, display 128 may configure an LED to display a blinking red color as well as configuring a buzzer (not shown) to produce an audible output. While the apparatus 100 (FIG. 1A) is in the low battery state, any in-progress measurements may be completed. After the measurement procedure is concluded, the DAQ/analysis controller 134 desirably permits only recharging of the battery.

During battery recharging, in an exemplary embodiment, the DAQ/analysis controller 134 configures an LED on the display 128 to emit a red color. The DAQ/analysis controller 134 desirably does not permit data acquisition during the recharging of the battery.

Although not illustrated in FIG. 11, an exemplary embodiment of the present invention further includes the capability by the DAQ/analysis controller 134 to determine whether the amplitude of the received PCG signal is saturated upon starting a data acquisition. If the PCG signal is saturated, the DAQ/analysis controller 134 may transmit a command to connection module 132, such as via a short-range transceiver, to adjust a gain within PCG signal conditioner 106. Although in an exemplary embodiment, saturation of the PCG signal received by the DAQ/analysis controller 134 is determined, it is contemplated that the DAQ/analysis controller 134 may determine whether the ECG signal is saturated, whether the PCG or ECG signal is too low, or any desirable combination of amplitude conditions.

Although the invention has been described in terms of apparatus and methods for noninvasively estimating a PAP, it is contemplated that one or more components may be implemented in software on microprocessors/general purpose computers (not shown). In this embodiment, one or more of the functions of the various components may be implemented in software that controls a general purpose computer. This software may be embodied in a computer readable carrier, for example, a magnetic or optical disk, a memory-card or an audio frequency, radio-frequency, or optical carrier wave.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A method for noninvasively estimating a blood pressure, the method comprising the steps of:
    a) extracting a pulmonic (P) component from a second heart sound (S2) signal;
    b) analyzing the extracted P component to obtain a number of oscillations in the P component;
    c) determining a value that corresponds to the number of oscillations; and
    d) applying a predetermined relationship between the value and blood pressure to generate a blood pressure estimate.

2. The method according to claim 1, wherein the blood pressure includes a pulmonary artery pressure (PAP) and step (d) includes applying the predetermined relationship between the value and PAP to generate a PAP estimate.

3. The method according to claim 1, the method further including the steps of, prior to step (a):
    receiving a phonocardiogram (PCG) signal; and
    extracting the S2 signal from the received PCG signal,
    wherein step (a) extracts the P component from the extracted S2 signal.

4. The method according to claim 1, wherein the S2 signal is a time-domain S2 signal and step (a) extracts the P component using the time-domain S2 signal.

5. The method according to claim 1, wherein step (b) determines the number of oscillations using a derivative with respect to time of the P component.

6. The method according to claim 1, wherein the predetermined relationship is determined by a linear regression between a plurality of measured numbers of oscillations and a respective plurality of measured blood pressures corresponding to the measured numbers of oscillations.

7. The method according to claim 1, step (a) includes the steps of:
    determining a P component onset time according to a maximum absolute value of a time derivative of the S2 signal; and
    selecting a predetermined portion of the S2 signal as the P component using the determined P component onset time.

8. The method according to claim 1, wherein the S2 signal includes a plurality of S2 signals, and
    step (a) includes extracting a corresponding plurality of P components from the plurality of S2 signals,
    wherein the blood pressure estimate is generated according to the extracted plurality of P components.

9. The method according to claim 8, further including the step of determining a confidence interval measure associated with the blood pressure estimate.

10. The method according to claim 8, further including the steps of:
    repeating steps (b), (c) and (d) over the plurality of S2 signals to generate a corresponding plurality of blood pressure estimates; and
    determining a mode of the plurality of blood pressure estimates to generate an average blood pressure estimate.

11. The method according to claim 8, further including the steps of:
    determining a mean S2 signal from the plurality of S2 signals; and
    repeating steps (b), (c) and (d) using the mean S2 signal to generate the blood pressure estimate.

12. The method according to claim 11, wherein the step of determining the mean S2 signal further includes the steps of:
    determining a plurality of discrete Fourier transform (DFT) signals corresponding to the plurality of S2 signals;
    computing a mean DFT signal from the plurality of DFT signals; and
    determining an inverse discrete Fourier transform (IFDT) signal from the mean DFT signal, the IFDT signal forming the mean S2 signal.

13. The method according to claim 1, the method further including the steps of, prior to step (a):
    synchronously receiving a phonocardiogram (PCG) signal and an electrocardiogram (ECG) signal for a predetermined duration of time; and
    extracting the S2 signal from the received PCG signal using the received ECG signal,
    wherein step (a) extracts the P component from the extracted S2 signal.

14. The method according to claim 13, the step of extracting the S2 signal includes the steps of:
    determining two consecutive QRS complex onset times from the received ECG signal;
    calculating a time interval from the determined QRS complex onset times;
    determining an S2 onset time according to the calculated time interval; and
    selecting a predetermined portion of the PCG signal using the determined S2 onset time as the extracted S2 signal.

15. The method according to claim 13, wherein the PCG signal includes a plurality of PCG signals and the ECG signal includes a plurality of ECG signals corresponding to the plurality of PCG signals, the step of synchronously receiving the PCG signal and the ECG signal includes synchronously receiving the plurality of PCG signals and the plurality of ECG signals, and the step of extracting the S2 signal includes extracting a corresponding plurality of S2 signals, wherein the blood pressure estimate is generated according to the extracted plurality of S2 signals.

16. The method according to claim 15, further including the step of determining a confidence interval measure associated with the blood pressure estimate.

17. The method according to claim 16, further including the step of storing at least one of the received PCG signal, the received ECG signal, the extracted S2 signal, the P component, the blood pressure estimate and the confidence interval measure.

18. The method according to claim 16, further including the step of presenting, on a display device, the blood pressure estimate and at least one of the received PCG signal, the received ECG signal, the extracted S2 signal, the P component and the confidence interval measure.

19. A non-transitory computer-readable medium including computer program instructions that cause a computer to perform a method for noninvasively estimating a blood pressure, the method comprising the steps of:
 a) extracting a pulmonic (P) component from a second heart sound (S2) signal;
 b) analyzing the extracted P component to obtain a number of oscillations in the P component;
 c) determining a value that corresponds to the number of oscillations; and
 d) applying a predetermined relationship between the value and blood pressure to generate a blood pressure estimate.

20. Apparatus for noninvasively estimating a blood pressure, the apparatus comprising:
 a) means for extracting a pulmonic (P) component from a second heart sound (S2) signal;
 b) means for analyzing the extracted P component to obtain a number of oscillations in the P component;
 c) means for determining a value that corresponds to the number of oscillations; and
 d) means for applying a predetermined relationship between the value and blood pressure to generate a blood pressure estimate.

21. Apparatus according to claim 20, wherein the blood pressure includes a pulmonary artery pressure (PAP) and the means for applying the predetermined relationship includes means for applying the predetermined relationship between the value and PAP to generate a PAP estimate.

22. Apparatus according to claim 20, the apparatus further comprising:
 means for receiving a phonocardiogram (PCG) signal; and
 means for extracting the S2 signal from the received PCG signal,
 wherein the means for extracting the P component includes means for extracting the P component from the extracted S2 signal.

23. Apparatus according to claim 20, the apparatus further comprising:
 means for synchronously receiving a phonocardiogram (PCG) signal and an electrocardiogram (ECG) signal for a predetermined duration of time; and
 means for extracting the S2 signal from the received PCG signal using the received ECG signal,
 wherein the means for extracting the P component includes means for extracting the P component from the extracted S2 signal.

* * * * *